(12) United States Patent
Gagliardi et al.

(10) Patent No.: US 6,506,758 B2
(45) Date of Patent: Jan. 14, 2003

(54) INDOLE DERIVATIVES USEFUL A.O. FOR THE TREATMENT OF OSTEOPOROSIS

(75) Inventors: Stefania Gagliardi, Como (IT); Guy Marguerite Marie Gerard Nadler, Rennes (FR); Pietro A T Novella, Milan (IT)

(73) Assignees: SmithKline Beecham Laboratoires Pharmceutiques, Nanterre Cedex (FR); SmithKline Beecham SpA, Milan (IT)

( * ) Notice: Subject to any disclaimer, the term of this patent is extended or adjusted under 35 U.S.C. 154(b) by 0 days.

(21) Appl. No.: 09/975,347

(22) Filed: Oct. 11, 2001

(65) Prior Publication Data

US 2002/0099080 A1 Jul. 25, 2002

Related U.S. Application Data

(63) Continuation of application No. 09/582,302, filed as application No. PCT/EP98/08561 on Dec. 17, 1998.

(30) Foreign Application Priority Data

Dec. 24, 1997 (EP) ............................................. 97403154

(51) Int. Cl.$^7$ ................... C07D 401/12; C07D 209/18; A61K 31/40
(52) U.S. Cl. .................. 514/254.09; 544/373; 514/415; 514/323; 548/511; 546/201
(58) Field of Search ..................... 544/373; 514/254.09, 514/415, 323; 548/511; 546/201

(56) References Cited

FOREIGN PATENT DOCUMENTS

| WO | WO 96/21644 | 7/1996 |
|----|-------------|--------|
| WO | WO 98/57952 | 12/1998 |

OTHER PUBLICATIONS

CAS printout for Kapuscinski et al.*
Scartoni et al., Nitrogen heterocycles. Part 7, some reaction of 2–anilinophthalimidine derivatives, J. Chem. Soc., 20:2332, 1977.*
Sakamoto et al., Preparation and palladium–catalysed arylation of indolylzinc halides, J. Chem. Soc., 1996.*
CAS printout for Schoen et al.*
Chemical Abstracts, 1997, vol. 127, No. 13, abstract No. 17108w.
Database Chemical Abstracts No. XP–002104816, 1997, vol. 8, No. 5. abstract No. 171080.
Chemical Abstracts, 1996, vol. 124, No. 25, abstract No. 343278y.
Database Chemical Abstracts No. XP–002104817, 1996, vol. 8, No. 5. abstract No. 343278.
Sakamoto et al., J. Chem. Soc. Perkin Trans. 1, 1996, pp. 1927–1934.
Chemical Abstracts, 1978, vol. 88, No. 7, abstract No. 46557g.
Database Chemical Abstracts No. XP–002104818, 1978, vol. 67, abstract No. 46557.
Scartoni, et al., J. Chem. Soc., 1977, vol. 20, Part 7, pp. 2332–2336.

* cited by examiner

*Primary Examiner*—Mukund J. Shah
*Assistant Examiner*—Hong Liu
(74) *Attorney, Agent, or Firm*—Laura K. Madden; Mary E. McCarthy; Charles M. Kinzig

(57) ABSTRACT

A compound of formula (I):

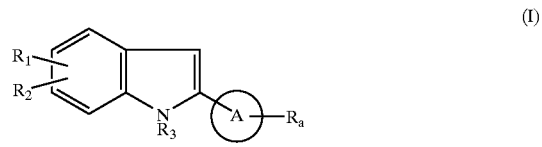

or a salt thereof, or a solvate thereof, wherein:

A represents an optionally substituted aryl group or an optionally substituted heterocyclyl group;

$R_a$ represents —CO—$NR_sR_t$ wherein $R_s$ and $R_t$ each independently represent hydrogen, alkyl, substituted alkyl, optionally substituted alkenyl, optionally substituted aryl, optionally substituted arylalkyl, optionally substituted heterocyclyl or an optionally substituted heterocyclylalkyl group, or $R_s$ and $R_t$ together with the nitrogen to which they are attached form a heterocyclyl group;

$R_1$ and $R_2$ each independently represents hydrogen, hydroxy, amino, alkoxy, optionally substituted aryloxy, optionally substituted benzyloxy, alkylamino, dialkylamino, halo, trifluoromethyl, trifluoromethoxy, nitro, alkyl, carboxy, carbalkoxy, carbamoyl, alkylcarbamoyl, or $R_1$ and $R_2$ together represent methylenedioxy, carbonyldioxy or carbonyldiamino; and $R_3$ represents hydrogen, alkanoyl, alkyl, aminoalkyl, hydroxyalkyl, carboxyalkyl, carbalkoxyalkyl, carbamoyl or alkylsulphonyl and arylsulphonyl; a process for the preparation of such a compound, a pharmaceutical composition containing such a compound and the use of such a compound or composition in medicine.

15 Claims, No Drawings

INDOLE DERIVATIVES USEFUL A.O. FOR THE TREATMENT OF OSTEOPOROSIS

This is a continuation of application Ser. No. 09/582,302 filed Jun. 22, 2000, which is a 371 of International Application No. PCT/EP98/08561, filed Dec. 17, 1998.

This invention relates to certain novel compounds, to a process for preparing such compounds, to pharmaceutical compositions containing such compounds and to the use of such compounds and compositions in medicine.

Diseases associated with loss of bone mass are known to be caused by over activity of osteoclast cells. It is also known that certain compounds, usually related to bafilomycin, are useful for treating such diseases: For example International Patent Application, publication number WO 91/06296 discloses certain bafilomycin macrolides for the treatment of bone affecting diseases.

However, bafilomycin derivatives are not selective for osteoclasts in humans. The use of these compounds is therefore associated with unacceptable toxicity due to generalised blockade of other essential v-ATPases. Indeed, to date there is no known treatment which is selective for the human osteoclasts.

The search for a successful treatment for diseases associated with loss of bone mass in humans is further complicated in that the nature of the therapeutic target for the selective inhibition of the osteoclasts is controversial. Thus Baron et al. (International Patent Application publication number WO93/01280) indicate that a specific vacuolar ATPase (V-ATPase) has been identified in osteoclasts as a potential therapeutic target. However, the Baron work was carried out in chickens and Hall et al (*Bone and Mineral* 27, 159–166, (1994)), in a study relating to mammals, conclude that in contrast to avian osteoclast V-ATPase, mammalian osteoclast V-ATPase is pharmacologically similar to the v-ATPase in other cells and, therefore, it is unlikely to be a good therapeutic target.

We have now found a group of compounds which are selective for mammalian osteoclasts, acting to selectively inhibit their bone resorbing activity. These compounds are therefore considered to be particularly useful for the treatment and/or prophylaxis of diseases associated with loss of bone mass, such as osteoporosis and related osteopenic diseases, Paget's disease, hyperparathyroidism and related diseases. These compounds are also considered to possess anti-tumour activity, antiviral activity (for example against Semliki Forest, Vesicular Stomatitis, Newcastle Disease, Influenza A and B, HIV viruses). antiulcer activity (for example the compounds may be useful for the treatment of chronic gastritis and peptic ulcer induced by *Helicobacter pylori*), immunosupressant activity, antilipidemic activity, antiatherosclerotic activity and to be useful for the treatment of AIDS and Alzheimer's disease. In a further aspect, these compounds are also considered useful in inhibiting angiogenesis, i.e. the formation of new blood vessels which is observed in various types of pathological conditions (angiogenic diseases) such as rheumatoid arthritis, diabetic retinopathy, psoriasis and solid tumours.

Accordingly, the invention provides a compound of formula (I):

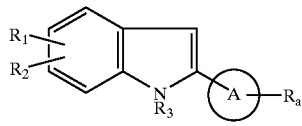

or a salt thereof, or a solvate thereof, wherein:

A represents an optionally substituted aryl group or an optionally substituted heterocyclyl group;

$R_a$ represents —CO—$NR_sR_t$ wherein $R_s$ and $R_t$ each independently represent hydrogen, alkyl, substituted alkyl, optionally substituted alkenyl, optionally substituted aryl, optionally substituted arylalkyl, optionally substituted heterocyclyl or an optionally substituted heterocyclylalkyl group, or $R_s$ and $R_t$ together with the nitrogen to which they are attached form a heterocyclyl group;.

$R_1$ and $R_2$ each independently represents hydrogen, hydroxy, amino, alkoxy, optionally substituted aryloxy, optionally substituted benzyloxy, alkylamino, dialkylamino, halo, trifluoromethyl, trifluoromethoxy, nitro, alkyl, carboxy, carbalkoxy, carbamoyl, alkylcarbamoyl, or $R_1$ and $R_2$ together represent methylenedioxy, carbonyldioxy or carbonyldiamino; and $R_3$ represents hydrogen, alkanoyl, alkyl, aminoalkyl, hydroxyalkyl, carboxyalkyl, carbalkoxyalkyl, carbamoyl or alkylsulphonyl and arylsulphonyl.

Examples of aryl groups represented by A include phenyl and naphthyl.

Examples of heterocyclyl groups represented by A include furyl groups.

Suitably, $R_1$ and $R_2$ each independently represents a halogen substituent, for example chloro.

Suitable positions for substitution for $R_1$ or $R_2$ are the 4, 5, 6 or 7 position. favourably the 5 or 6 position.

In a preferred aspect $R_1$ is chloro, especially 5-chloro. and $R_2$ is chloro, especially 6-chloro.

Suitably, $R_3$ represents hydrogen.

When $R_s$ or $R_t$ represent alkyl or substituted alkyl, suitable alkyl groups are $C_{1-6}$ alkyl groups, for example $C_1$, $C_2$, $C_3$, $C_4$ and $C_5$ alkyl groups, favourably ethyl, propyl or butyl.

When $R_s$ or $R_t$ represent substituted alkyl, favoured groups are 2-(dialkylamino)ethyl, 3-(dialkylamino)propyl, 4-(dialkylamino)butyl, 3-[4-(3-chlorophenyl)piperazin-1-yl]propyl, 3-[4-(3-hydroxyphenyl)piperazin-1-yl]propyl, heterocyclylmethyl, heterocyclylethyl or heterocyclylpropyl groups.

Suitably, $R_s$ represents optionally substituted heterocyclyl, and aryl.

Suitably, $R_s$ represents optionally substituted heterocyclylalkyl.

Suitably, $R_t$ is hydrogen.

In a favoured aspect, $R_s$ represents an optionally substituted piperidinyl group, especially a 4-piperidinyl group.

Subsituents for the piperidinyl ring include alkyl, fused cycloalkyl and hydroxyalkyl, polyhydroxyalkyl.

Favoured substituents for piperidinyl groups are alkyl groups.

When the piperidinyl group is substituted it is preferred if the substituents are attached to one or both of the carbon atoms alpha to the nitrogen atom.

An example of a substituted piperidinyl groups is a 1,2,2,6,6-pentamethylpiperidin-4-yl group and 2,2,6,6-tetramethylpiperidin4-yl.

When $R_s$ represents heterocyclylalkyl, suitable heterocyclyl groups are optionally substituted saturated single ring heterocyclic group having 5 to 8, preferably 5 or 6, ring atoms, which atoms include 1, 2 or 3 heteroatoms selected from O, S, or N; for example an optionally substituted piperazinyl group; Suitable optional substituents for the heterocyclyl groups are optionally substituted aryl groups, for example hydroxyphenyl or chlorophenyl groups.

There is a moiety, referred to herein as moiety (b), which forms part of formula (I) and which has the formula shown below:

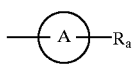

(b)

In one preferred aspect moiety (b) represents a moiety of formula (c):

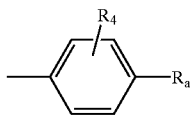

(c)

wherein $R_a$ is as defined relation to formula (I) and $R_4$ represents hydrogen, hydroxy, alkoxy, alkythio, halogen or a group $NR_uR_v$ wherein $R_u$ and $R_v$ each independently represent hydrogen, alkyl or alkylcarbonyl.

Suitably $R_4$ is located meta to $R_a$.

Suitably, $R_4$ represents hydrogen or alkoxy, preferably alkoxy.

An example of $R_4$ is hydrogen. An example of $R_4$ is methoxy.

Particular examples of formula (I) are those of example numbers 2, 7 and 8.

As used herein, the term "alkyl" includes straight or branched chain alkyl groups having from 1 to 12, suitably 1 to 6, preferably 1 to 4, carbon atoms, such as methyl, ethyl, n- and iso-propyl and n- iso-, tert-butyl and pentyl groups, and also includes such alkyl groups when forming part of other groups such as alkoxy or alkanoyl groups.

As used herein, the term "aryl" includes phenyl and naphthyl, especially phenyl.

Suitable optional substituents for any aryl group include up to 5 substituents, suitably up to 3 substituents, selected from alkyl, alkoxy, thioalkyl, hydroxy, halogen, trifluoromethyl, alkylcarbonyl, cyano, nitro, or a group $NR_uR_v$ wherein $R_u$ and $R_v$ each independently represent hydrogen, alkyl or alkylcarbonyl.

Suitable arylalkyl groups include aryl-$C_{1-3}$-alkyl groups such as phenylethyl and benzyl groups, especially benzyl.

Preferably, substituted aralkyl groups are substituted in the aryl moiety.

As used herein, the term "heterocyclyl" includes saturated or unsaturated single or fused ring heterocyclic groups, each ring having 4 to 11 ring atoms, especially 5 to 8, preferably 5, 6 or 7 which ring atoms include 1, 2 or 3 heteroatoms selected from O, S, or N.

Suitable optional substituents for any heterocyclyl group includes those mentioned herein with repect to the aryl group.

As used herein, the term "halogen" or "halo" includes fluoro, chloro, bromo and iodo, suitably fluoro and chloro, favourably chloro.

When used herein "acyl" includes alkyl carbonyl.

Certain of the carbon atoms of the compounds of formula (I) are chiral carbon atoms and may therefore provide stereoisomers of the compound of formula (I). The invention extends to all stereoisomeric forms of the compounds of formula (I) including enantiomers and mixtures thereof, including racemates. The different stereoisomeric forms may be separated or resolved one from the other by conventional methods or any given isomer may be obtained by conventional stereospecific or asymmetric syntheses.

Suitable salts are pharmaceutically acceptable salts.

Suitable pharmaceutically acceptable salts include acid addition salts and salts of carboxy groups.

Suitable pharmaceutically acceptable acid addition salts include salts with inorganic acids such, for example, as hydrochloric acid, hydrobromic acid, orthophosphoric acid or sulphuric acid, or with organic acids such, for example as methanesulphonic acid, toluenesulphonic acid, acetic acid, propionic acid, lactic acid, citric acid, fumaric acid, malic acid, succinic acid, salicylic acid, maleic acid, glycerophosphoric acid or acetylsalicylic acid.

Suitable pharmaceutically acceptable salts of carboxy groups include metal salts, such as for example alumninium, alkali metal salts such as sodium or potassium and lithium, alkaline earth metal salts such as calcium or magnesium and ammonium or substituted ammonium salts, for example those with C1-6 alkylamines such as triethylamine, hydroxy-C1-6 alkylamines such as 2-hydroxyethylamine, bis-(2-hydroxyethyl)-amine or tri-(2-hydroxyethyl)-amine, cycloalkylamines such as dicyclohexylamine, or with procaine, 1,4-dibenzylpiperidine, N-benzyl-b-phenethylamine, dehydroabietylamine, N,N'-bisdehydroabietylamine, glucamine, N-methylglucamine or bases of the pyridine type such as pyridine, collidine or quinoline.

Suitable solvates of the compounds of the formula (I) are pharmaceutically acceptable solvates, such as hydrates.

The salts and/or solvates of the compounds of the formula (I) which are not pharmaceutically acceptable may be useful as intermediates in the preparation of pharmaceutically acceptable salts and/or solvates of compounds of formula (I) or the compounds of the formula (I) themselves, and as such form another aspect of the present invention.

A compound of formula (I) or a salt thereof or a solvate thereof may be prepared by amidation of a compound of formula (II):

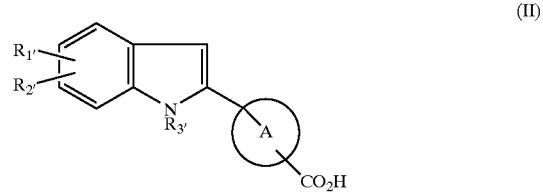

(II)

wherein A is as defined in relation to formula (I), $R_{1'}$, $R_{2'}$, and $R_{3'}$ each respectively represent $R_1$, $R_2$ and $R_3$ as defined in relation to formula (I) or a protected form thereof; and thereafter, as necessary, carrying out one or more of the following reactions:

(i) converting one compound of formula (I) into another compound of formula (I);

(ii) removing any protecting group;

(iii) preparing a salt or a solvate of the compound so formed.

Suitable amidation methods include treating the compound of formula (II) with a compound of formula (III):

   (III)

wherein $R_s$ and $R_t$ are as defined in relation to formula (I); and thereafter, as required, removing any protecting group from the compound so formed.

The reaction between the compounds of formula (II) and (III) may be carried out under the appropriate conventional amidation conditions, for example in an aprotic solvent such as dimethylformamide, at any temperature providing a suitable rate of formation of the required product, conveniently at ambient temperature; preferably the amidation reaction is carried out in the presence of a peptide coupling reagent such as 1-hydroxy-7-azabenzotriazole (HOAT), and/or 1-(3-dimethylaminopropyl)-3-ethylcarbodiimide hydrochloride (WSC).

A compound of formula (II) may be prepared by cyclising a compound of formula (IV):

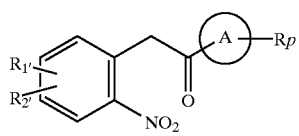   (IV)

wherein A, $R_{1'}$ and $R_{2'}$ are as defined in relation to formula (II) and $R_p$ represents a protected carboxyl group or a group convertible into a carboxyl group; and thereafter, as required, converting the group $R_p$ into a carboxyl group.

Suitably, the cyclisation reaction is carried out under reductive cyclisation conditions, for example by using powdered iron/acetic acid mixtures or an alkali metal hydrogensulphite, such as sodium hydrogensulphite, in any suitable solvent such as tetrahydrofuran, ethanol, methanol or water or mixtures thereof at any temperature providing a suitable rate of formation of the required product, such as an elevated temperature conveniently at the reflux temperature of the solvent.

When $R_p$ is a protecting group, suitable protecting groups include lower alkyl groups, for example methyl or ethyl groups, which may be removed by conventional hydrolysis methods, for example by use of basic hydrolysis using ethanolic potassium hydroxide.

When $R_p$ is a group convertible into a carboxyl group, suitable groups include cyano groups: Such groups may be converted into carboxyl groups using conventional methods for example when $R_p$ is a cyano group it may be converted into a carboxyl group by hydrolysis using conventional methods, for example by use of basic hydrolysis using potassium hydroxide solution in ethanol at reflux. A preferred value of $R_p$ is a cyano group.

A compound of formula (IV) is prepared by reacting a compound of formula (V):

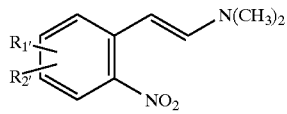   (V)

wherein $R_{1'}$ and $R_{2'}$ are as defined in relation to formula (II) with a compound of formula (VI):

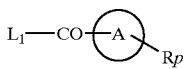   (VI)

wherein A and $R_p$ are as defined in relation to formula (IV) and $L_1$ represents a leaving group or atom, such as a halogen atom, for example a chlorine atom.

The reaction between the compounds of formula (V) and (VI) may be carried out in an inert hydrocarbon solvent, such as cyclohexane. at any temperature providing a suitable rate of formation of the required product, preferably at an elevated temperature, such as the reflux temperature of the solvent and in presence of a base, preferably a tertiary amine such as triethylamine.

The reaction between the compounds of formulae (V) and (VI) proceeds via an intermediate which is not usually isolated and which provides the required compound of formula (IV) on heating in situ. It an alternative aspect, the intermediate is isolated thereby providing an alternative preparation of the compound of formula (IV) wherein the compound of formula (VII):

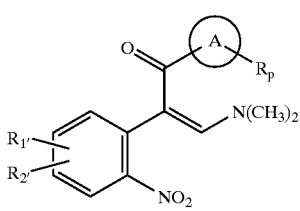   (VII)

wherein A, $R_{1'}$ and $R_{2'}$ are as defined in relation to formula (II) and $R_p$ is as defined in relation to formula (IV), is heated to provide the herein before defined compound of formula (IV).

The conversion of compound (VII) into the compound of formula (IV) is conveniently carried out in a polar solvent mixture, such as dioxane and water, usually at the reflux temperature of the solvent mixture in conditions analogous to those described in *J. Het. Chem.* 11, 219–221, (1974).

The compounds of formula (V) are known compounds or they are prepared using methods analogous to those used to prepare known compounds, such as those disclosed by Meervein et al *Ann. Chem.* 641, 1 (1961) and Org. Synth. Collective VII, 34–41.

The compounds of formula (III) are known or they are prepared using methods analogous to those used to prepare known compounds, such as those described in J. March, *Advanced Organic Chemistry,* 3rd Edition (1985), Wiley Interscience.

Suitable conversions of one compound of formula (I) into another compound of formula (I) includes converting a compound of formula (I) wherein $R_3$ is H into $R_3$ is other than H, for example lower alkyl or carboxyalkyl The conversion of one compound of formula (I) into another compound of formula (I) may be carried out using the appropriate conventional procedure; for example the above mentioned conversion (i) (of $R_3$ as H into $R_3$ as other than H) may be carried out by reacting the compound of formula (I) with a strong base. for example sodium hydride in a solvent such as dimethylformamide, followed by alkylation with an alkyl halide or alkyl sulphate or acylation with an acyl halide. Alternatively, the conversion of $R_3$ as H into $R_3$ as other than H may be carried out by reacting the compound of formula (I) with a finely grounded solid base, for example potassium hydroxide, in a solvent such as acetone, followed by alkylation with an alkyl halide or acylation with an acyl halide.

Amines of general formula HNRsRt may be prepared using the methods known in the art for the preparation of amines, for example as taught in *Houben-Weil, Methoden der Organischen Chemie,* Vol. XI/1 (1957) and Vol. E16d/2(1992), Georg Thieme Verlag, Stuttgart.

A compound of formula (I) or a solvate thereof may be isolated from the above mentioned processes according to standard chemical procedures.

The preparation of salts and/or solvates of the compounds of formula (I) may be performed using the appropriate conventional procedure.

If required mixtures of isomers of the compounds of the invention may be separated into individual stereoisomers and diastereoisomers by conventional means, for example by the use of an optically active acid as a resolving agent. Suitable optically active acids which may be used as resolving agents are described in *"Topics in Stereochemistry",* Vol. 6, Wiley Interscience, 1971, Allinger, N. L. and Eliel, W. L. Eds.

Alternatively, any enantiomer of a compound of the invention may be obtained by stereospecific synthesis using optically pure starting materials of known configuration.

The absolute configuration of compounds may be determined by conventional methods such as X-ray crystallographic techniques.

The protection of any reactive group or atom, may be carried out at any appropriate stage in the aforementioned processes. Suitable protecting groups include those used conventionally in the art for the particular group or atom being protected. Protecting groups may be prepared and removed using the appropriate conventional procedure, for example OH groups, including diols, may be protected as the silylated derivatives by treatment with an appropriate silylating agent such as di-tert-butylsilylbis (trifluoromethanesulfonate): the silyl group may then be removed using conventional procedures such as treatment with hydrogen fluoride preferably in the form of a pyridine complex and optionally in the presence of alumina or by treatment with acetyl chloride in methanol. Alternatively benzyloxy groups may be used to protect phenolic groups, the benzyloxy group may be removed using catalytic hydrogenolysis using such catalysts as palladium (II) chloride or 10% palladium on carbon.

Amino groups may be protected using any conventional protecting group, for example tert-butyl esters of carbamic acid may be formed by treating the amino group with di-tert-butyldicarbonate, the amino group being regenerated by hydrolysing the ester under acidic conditions, using for example hydrogen chloride in aqueous ethanol or trifluoroacetic acid in methylene dichloride. An amino group may be protected as a benzyl derivative, prepared from the appropriate amine and a benzyl halide under basic conditions, the benzyl group being removed by catalytic hydrogenolysis, using for example a palladium on carbon catalyst.

Indole NH groups and the like may be protected using any conventional group, for example benzenesulphonyl, methylsulphonyl, tosyl, formyl, acetyl (all of them removable by treatment with alkaline reagents), benzyl (removable either with sodium in liquid ammonia or with Al Cl3 in toluene), allyl (removable by treatment with rhodium (III) chloride under acidic conditions), benzyloxycarbonyl (removable either by catalytic hydrogenation or by alkaline treatment), trifluoroacetyl (removable by either alkaline or acidic treatment), t-butyldimethylsilyl (removable by treatment with tetrabutylammonium fluoride), 2-(trimethylsilyl) ethoxymethyl (SEM) (removable by treatment with tetrabutylamnmonium fluoride in the presence of ethylendiamine), methoxymethyl (MOM) or methoxyethyl (MEM) groups (removed by mild acidic treatment).

Carboxyl groups may be protected as alkyl esters, for example methyl esters, which esters may be prepared and removed using conventional procedures, one convenient method for converting carbomethoxy to carboxyl is to use aqueous lithium hydroxide.

A leaving group or atom is any group or atom that will, under the reaction conditions, cleave from the starting material, thus promoting reaction at a specified site. Suitable examples of such groups unless otherwise specified are halogen atoms, mesyloxy, p-nitrobenzensulphonyloxy and tosyloxy groups.

The salts, esters, amides and solvates of the compounds mentioned herein may as required be produced by methods conventional in the art: for example, acid addition salts may be prepared by treating a compound of formula (I) with the appropriate acid.

Esters of carboxylic acids may be prepared by conventional esterification procedures, for example alkyl esters may be prepared by treating the required carboxylic acid with the appropriate alkanol, generally under acidic conditions.

Amides may be prepared using conventional amidation procedures, for example amides of formula $CONR_sR_t$ may be prepared by treating the relevant carboxylic acid with an amine of formula $HN\ R_s\ R_t$ wherein $R_s$ and $R_t$ are as defined above. Alternatively, a $C_{1-6}$ alkyl ester such as a methyl ester of the acid may be treated with an amine of the above defined formula $HNR_sR_t$ to provide the required amide, optionally in presence of trimethylalluminium following the procedure described in *Tetrahedron Lett.* 48, 4171–4173, (1977).

As mentioned above the compounds of the invention are indicated as having useful therapeutic properties:

The present invention therefore provides a method for the treatment and/or prophylaxis of diseases associated with over activity of osteoclasts in mammals which method comprises the administration of an effective non-toxic amount of a compound of formula (I), or a pharmaceutically acceptable salt thereof, or a pharmaceutically acceptable solvate thereof.

Thus, the present invention further provides a method for the treatment of osteoporosis and related osteopenic diseases in a human or non-human mammal, which comprises administering an effective, non-toxic, amount of a compound of formula (I) or a pharmaceutically acceptable solvate thereof, to a human or non-human mammal in need thereof.

In a further aspect, the present invention a compound of formula (I) or a pharmaceutically acceptable salt thereof, or a pharmaceutically acceptable solvate thereof, for use as an active therapeutic substance.

In particular the present invention provides a compound of formula (I) or a pharmaceutically acceptable salt thereof and/or a pharmaceutically acceptable solvate thereof, for use in the treatment of and/or prophylaxis of osteoporosis and related osteopenic diseases.

Of particular interest is the osteoporosis associated with the peri and post menopausal conditions. Also encompassed are the treatment and prophylaxis of Paget's disease, hypercalcemia associated with bone neoplasms and all the types of osteoporotic diseases as classified below according to their etiology:

Primary Osteoporosis
  Involutional
    Type I or postmenopausal
    Type II or senile
    Juvenile
    Idiopathic in young adults
Secondary Osteoporosis
  Endocrine abnormality
    Hyperthyroidism
    Hypogonadism
    Ovarian agenesis or Turner's syndrome
    Hyperadrenocorticism or Cushing's syndrome
    Hyperparathyroidism
  Bone marrow abnormalities
    Multiple myeloma and related disorders
    Systemic mastocytosis
    Disseminated carcinoma
    Gaucher's disease
  Connective tissue abnormalities
    Osteogenesis imperfecta
    Homocystinuria
    Ehlers-Danlos syndrome
    Marfan's syndrome
    Menke's syndrome
  Miscellaneous causes
    Immobilisation or weightlessness
    Sudeck's atrophy
    Chronic obstructive pulmonary disease
    Chronic alcoholism
    Chronic heparin administration
    Chronic ingestion of anticonvulsant drugs In addition the invention encompasses the treatment of tumours, especially those related to renal cancer, melanoma, colon cancer, lung cancer and leukemia, viral conditions (for example those involving Semliki Forest virus, Vesicular Stomatitis virus, Newcastle Disease virus, Influenza A and B viruses, HIV virus), ulcers (for example chronic gastritis and peptic ulcer induced by *Helicobacter pylori*), for use as immunosupressant agents in autoimmune diseases and transplantation, antilipidemic agents for the treatment and/or prevention of hypercholesterolemic and atherosclerotic diseases and to be useful for the treatment of AIDS and Alzheimer's disease. These compounds are also considered useful in treating angiogenic diseases, i.e. those pathological conditions which are dependent on angiogenesis, such as rheumatoid arthritis, diabetic retinopathy, psoriasis and solid tumours.

A compound of formula (I), or a pharmaceutically acceptable salt thereof and/or a pharmaceutically acceptable solvate thereof, may be administered per se or, preferably, as a pharmaceutical composition also comprising a pharmaceutically acceptable carrier.

Accordingly, the present invention also provides a pharmaceutical composition comprising a compound of formula (I), or a pharmaceutically acceptable salt thereof, or a pharmaceutically acceptable solvate thereof, and a pharmaceutically acceptable carrier therefor.

Active compounds or a pharmaceutically acceptable salt thereof and/or a pharmaceutically acceptable solvate thereof is normally administered in unit dosage form.

An amount effective to treat the disorders hereinbefore described depends upon such factors as the efficacy of the active compounds, the particular nature of the pharmaceutically acceptable salt or pharmaceutically acceptable solvate chosen, the nature and severity of the disorders being treated and the weight of the mammal. However, a unit dose will normally contain 0.01 to 50 mg, for example 1 to 25 mg, of the compound of the invention. Unit doses will normally be administered once or more than once a day, for example 1, 2, 3, 4, 5 or 6 times a day, more usually 1 to 3 or 2 to 4 times a day such that the total daily dose is normally in the range, for a 70 kg adult of 0.01 to 250 mg, more usually 1 to 100 mg, for example 5 to 70 mg, that is in the range of approximately 0.0001 to 3.5 mg/kg/day, more usually 0.01 to 1.5 mg/kg/day, for example 0.05 to 0.7 mg/kg/day.

The present invention also provides a method for the treatment of tumours, especially those related to renal cancer, melanoma, colon cancer, lung cancer and leukemia, viral conditions (for example those involving Semliki Forest, Vesicular Stomatitis, Newcastle Disease, Influenza A and B, HIV viruses), ulcers (for example chronic gastritis and peptic ulcer induced by *Helicobacter pylori*), autoimmune diseases and transplantation, for the treatment and/or prevention of hypercholesterolemic and atherosclerotic diseases. AIDS and Alzheimer's disease, angiogenic diseases, such as rheumatoid arthritis, diabetic retinopathy, psoriasis and solid tumours, in a human or non-human mammal, which comprises administering an effective, non-toxic, amount of a compound of formula (I) or a pharmaceutically acceptable solvate thereof, to a human or non-human mammal in need thereof.

In such treatments the active compound may be administered by any suitable route, e.g. by the oral, parenteral or topical routes. For such use, the compound will normally be employed in the form of a pharmaceutical composition in association with a human or veterinary pharmaceutical carrier, diluent and/or excipient. although the exact form of the composition will naturally depend on the mode of administration.

Compositions are prepared by admixture and are suitably adapted for oral, parenteral or topical administration. and as such may be in the form of tablets, capsules, oral liquid preparations, powders, granules, lozenges, pastilles, reconstitutable powders, injectable and infusable solutions or suspensions, suppositories and transdermal devices. Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants. disintegrants, colourants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

These solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

For parenteral administration, fluid unit dose forms are prepared containing a compound of the present invention and a sterile vehicle. The compound, depending on the vehicle and the concentration can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the active compound.

For topical administration, the composition may be in the form of a transdermal ointment or patch for systemic delivery of the active compound and may be prepared in a conventional manner, for example, as described in the standard textbooks such as 'Dermatological Formulations'—B. W. Barry (Drugs and the Pharmaceutical Sciences-Dekker) or Harrys Cosmeticology (Leonard Hill Books).

The present invention also provides the use of a compound of formula (I), or a pharmaceutically acceptable salt thereof, or a pharmaceutically acceptable solvate thereof, for the manufacture of a medicament for the treatment and/or prophylaxis of diseases associated with over activity of osteoclasts in mammals, such as the treatment and/or prophylaxis of osteoporosis and related osteopenic diseases.

The present invention also provides the use of a compound of formula (I), or a pharmaceutically acceptable salt thereof, or a pharmaceutically acceptable solvate thereof, for the manufacture of a medicament for the treatment of tumours, especially those related to renal cancer, melanoma, colon cancer, lung cancer and leukemia, viral conditions (for example those involving Semliki Forest, Vesicular Stomatitis, Newcastle Disease, Influenza A and B, HIV viruses), ulcers (for example chronic gastritis and peptic ulcer induced by *Helicobacter pylori*), autoimmune diseases and transplantation, for the treatment and/or prevention of hypercholesterolemic and atherosclerotic diseases, AIDS and Alzheimer's disease, angiogenic diseases, such as rheumatoid arthritis, diabetic retinopathy, psoriasis and solid tumours.

No unacceptable toxicological effects are expected with compounds of the invention when administered in accordance with the invention. As is common practice, the compositions will usually be accompanied by written or printed directions for use in the medical treatment concerned.

The following, descriptions, examples and pharmacological methods illustrate the invention but do not limit it in any way.

EXAMPLES AND DESCRIPTIONS

Description 1: trans-4,5-Dichloro-2-nitro-β-dimethylaminostyrene

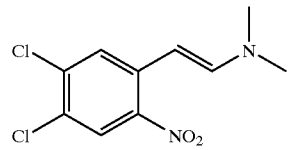

A solution of 10.3 g (50 mmol) of 4,5-dichloro-2-nitrotoluene (*Helv. Chim. Acta* 1936, 19, 434–439) in a mixture of 11.9 g (100 mmol) N,N-dimethylformamide dimethylacetal in DMF (25 ml) was heated at 100° C. for 16 h. The dark reaction mixture was concentrated in vacuo, the residue diluted with methylene chloride and washed twice with water. The organic solution was dried over $MgSO_4$, concentrated in vacuo affording 12.6 g (48 mmol, yield 96.5%) of the title compound as dark red to crude crystals.

Description 2: Methyl 4-[2-[(4,5-dichloro-2-nitro)phenyl]-1-oxo-ethyl]benzoate

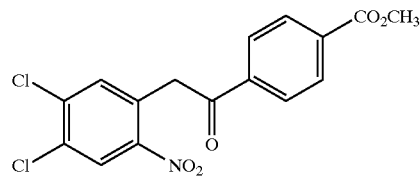

To a stirred solution of of trans-4,5-dichloro-2-nitro-β-dimethylaminostyrene (3.65 g, 14 mmol) and triethylamine (1.4 g, 14 mmol) in cyclohexane (20 ml), methyl terephthalic chloride (2.8 g, 14 mmol) was added portionwise. The resultant mixture was stirred and heated under reflux for 16 h. Sufficient water was then added to dissolve the salts formed and the organic layer was separated. The aqueous phase was extracted 3 times with ethyl acetate; the organic phases were pooled, washed with water and concentrated in vacuo. The residue was dissolved in a mixture of dioxane (30 ml) and water (20 ml) and the resultant solution was heated under reflux for 14 h and concentrated. The residue was dissolved in methylene chloride, washed with water, dried over $MgSO_4$ and concentrated in vacuo. The crude compound was purified by column chromatography ($SiO_2$; $CH_2Cl_2$) affording 2.7 g of the title compound (7.3 mmol, yield 52%).

$^1$H NMR(CDCl$_3$) δ=8.32 (s, 1H); 8.18 (d, 2H); 8.06 (d, 2H); 7.48 (s, 1H); 4.72 (s, 2H); 3.97 (s, 3H).

Description 3: Methyl 4-(5,6-dichloro-1H-indol-2-yl)benzoate

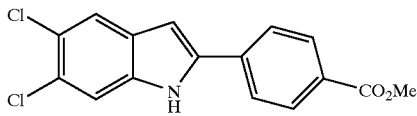

To a solution of methy 4-[2-[(4,5-dichloro-2-nitro)phenyl]-1-oxo-ethyl] benzoate (2.7 g, 7.3 mmol))in a mixture of THF (20 ml), ethanol (20 ml) and water (15 ml), sodium hydrosulfite (2.9 g, 7.9 mmol) was added portionwise. The mixture was heated for 15 min at reflux and stirring was continued at room temperature for 15 min. More sodium hydrosulfite was added and, after 5 min, warming the mixture was stirred at room temperature for additional 15 min and evaporated in vacuo to remove the organic solvents. The solid which separated was filtered, washed with water and dried to afford 0.9 g of the desired compound (2.8 mmol, yield 38%).

$^1$H NMR(DMSO-$d_6$) δ=12.05 (s, 1H); 8.03 (m, 4H); 7.84 (s, 1H); 7.61 (s, 1H); 7.09 (s, 1H); 3.88 (s, 3H)

Description 4: 4-(5,6-Dichloro-1H-indol-2-yl)benzoic acid

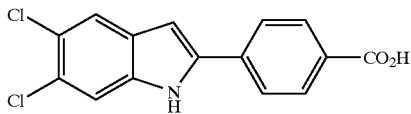

A solution of methyl 4-(5,6-dichloro-1H-indol-2-yl)benzoate (0.86 g, 2.7 mmol) and KOH (0.36 g, 6.4 mmol) in a mixture of EtOH (15 ml) and water (15 ml) was refluxed for 3 h. After concentration of the ethanol, the solution was acidified and extracted with ethyl acetate. The organic phase was washed with water, dried over MgSO$_4$ and concentrated in vacuo to afford 0.58 g (1.8 mmol, yield 70%) of the acid used without further purification.

$^1$H NMR(DMSO-$d_6$) δ=12.03 (s, 1H); 8.02 (m, 4H); 7.83 (s, 1H); 7.61 (s, 1H); 7.07 (s, 1H).

Description 5: 2-Methoxy-1,4-benzenedicarboxylic acid monoethylester and 3-Methoxy-1,4-benzenedicarboxylic acid monoethylester (Respectively A and B)

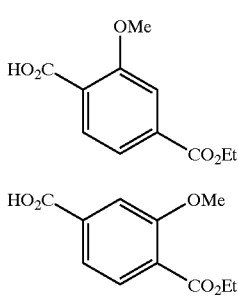

A mixture of dimethyl 2-methoxy-1,4-benzenedicarboxylate (5.8 g, 26 mmol), KOH (1.7g, 26 mmol) in EtOH (120 ml) was refluxed for 16 h. The solvent was concentrated, the residue was dissolved in water and the aqueous phase was washed twice with AcOEt. The aqueous solution was acidified with HCl and extracted three times with methylene chloride. The organic phase was dried over MgSO$_4$ and concentrated. The residue was purified by flash chromatography (SiO$_2$; CH$_2$Cl$_2$—MeOH : 9-1) to afford a 50/50 mixture of 2-methoxy-1,4-benzenedicarboxylic acid monoethylester and 3-methoxy-1,4-benzenedicarboxylic acid monoethylester (3.5 g, 17.5 mmol, yield 67%).

Description 6: Ethyl 2-methoxy-1,4-benzenedicarboxylic acid chloride and Ethyl 3-methoxy-1,4-benzenedicarboxylic acid chloride (Respectively A and B)

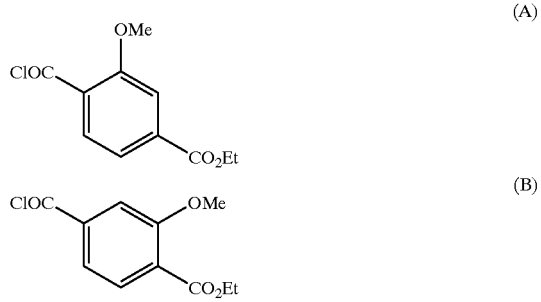

The mixture of 2-methoxy-1,4-benzenedicarboxylic acid monoethylester and 3-methoxy-1,4-benzenedicarboxylic acid monoethyl ester (3.5 g, 17.5 mmol) was dissolved in methylene chloride (20 ml) containing one drop of DMF. Oxalyl chloride (2.7 g, 21 mmol) was added dropwise at room temperature and stirring was continued for 2 h. The solvent and the excess of reagent were concentrated under reduced pressure; cyclohexane was added to the residue and then concentrated to flush the last traces of reagent. The mixture was used in the next step without further purification.

Description 7: Ethyl 3-methoxy-4-[2-[(4,5-dichloro-2-nitro)phenyl]-1-oxo-ethyl]-benzoate and ethyl 2-methoxy-4-[2-[(4,5-dichloro-2-nitro)phenyl]-1-oxo-ethyl]-benzoate (Respectively A and B)

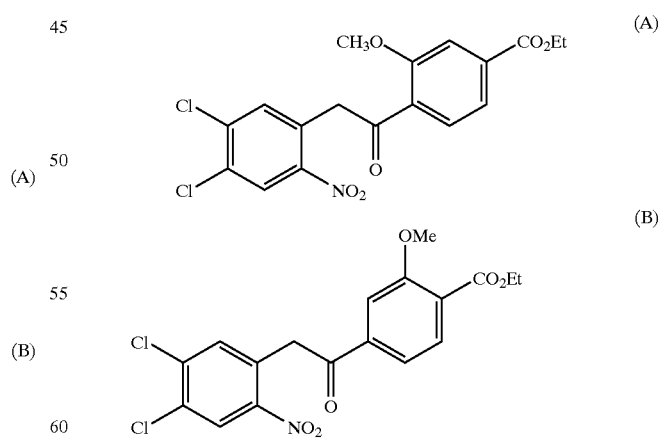

The crude mixture of acid chlorides obtained as above was added, at room temperature, to a stirred solution of trans-4,5-dichloro-2-nitro-β-dimethylaminostyrene (4.3 g, 16 mmol) and triethylamine (2.3 ml, 16 mmol) in of cyclohexane (35 ml). The mixture was heated 16 h at reflux and the solvent was then concentrated. The residue was dissolved in methylene chloride, washed with water, dried over MgSO₄ and concentrated in vacuo.

The residue was dissolved in dioxane (40 ml) and water (24 ml) was added. The mixture was refluxed for 24 h. The dioxane was concentrated, methylene chloride was added and the organic phase was washed with water, dried over MgSO₄ and concentrated in vacuo. The crude compound was purified by flash chromatography (SiO₂; CH₂Cl₂) affording 3.6 g of the title mixture (8.7 mmol, yield 53%).

Description 8: Ethyl 2-methoxy-4-(5,6-dichloro-1H-indol-2-yl)-benzoate and Ethyl 3-methoxy-4-(5,6-dichloro-1H-indol-2-yl)-benzoate (Respectively A and B)

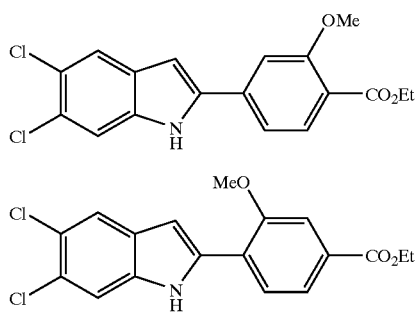

The mixture of ethyl 3-methoxy-4-[2-[(4,5-dichloro-2-nitro)phenyl]-1-oxo-ethyl]-benzoate and ethyl 2-methoxy-4-[2-[(4,5-dichloro-2-nitro)phenyl]-1-oxo-ethyl]-benzoate (3.6 g. 8.7 mmol) was treated with acetic acid (50 ml) and iron powder (1.5 g, 26 mmol) and was refluxed for 4 h. The acetic acid was concentrated in vacuo and the residue was dissolved in ethyl acetate, washed twice with diluted aqueous HCl then with water. The organic phase was dried over MgSO₄ and concentrated in vacuo.

The residue was purified by flash chromatography (150 g SiO₄; CH₂Cl₂) affording 1.3 g (3.5 mmol, yield 40%) of ethyl 2-methoxy-4-(5,6-dichloro-1H-indol-2-yl)-benzoate (A) and 1 g (2.7 mmol, yield 31%) of ethyl 3-methoxy-4-(5,6-dichloro-1H-indol-2-yl)-benzoate (B).

A ¹H NMR(CDCl₃) δ=8.96 (broad s, 1H); 7.86 (d, 1H); 7.69 (s, 1H); 7.53 (s, 1H); 7.24 (d, 1H); 7.16 (s, 1H); 6.79 (d, 1H); 4.40 (q, 2H); 3.81 (s, 3H); 1.41 (t, 3H).

B ¹H NMR(CDCl₃) δ=9.77 (broad s, 1H); 7.85 (d, 1H); 7.73 (m, 3H); 7.53 (s, 1H); 6.91 (d, 1H); 4.41 (q, 2H); 4.10 (s, 3H); 1.43 (t, 3H).

Description 9: 3-Methoxy-4-(5,6-dichloro-1H-indol-2-yl)-benzoic acid

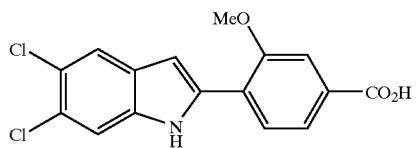

Ethyl 3-methoxy-4-(5,6-dichloro-1H-indol-2-yl)-benzoate (1 g, 2.7 mmol) was added to a solution of KOH (0.4 g, 7 mmol) in EtOH (50 ml) and the mixture was refluxed for 4 h. The solvent was concentrated and the residue was dissolved in water. The aqueous solution was acidified with HCl then extracted with AcOEt. The organic phase was washed with water, dried over MgSO₄ and concentrated in vacuo yielding 0.89 g (2.6 mmol, yield 99%) of the title compound.

¹H NMR(DMSO-d₆) δ=11.60 (broad s, 1H); 7.92 (d, 1H); 7.83 (s, 1H); 7.66 (m, 3H); 7.10 (s, 1H); 4.02 (s, 3H).

Description 10: 2-Methoxy-4-cyanobenzoyl chloride

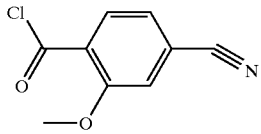

2-Methoxy-4-cyanobenzoic acid (*Tetrahedron Letters*, 1986, 27(49), 5997–6000) (1 g, 5.6 mmol) was dissolved in CH₂Cl₂ (20 ml). Oxalyl chloride (1.5 ml, 8.2 mmol) was rapidly introduced into the solution and a drop of DMF was added. A vigorous reaction took place with the abundant evolution of gaseous products. The solution was stirred for 1 h then allowed to stand over night. Solvent was removed using a rotary evaporator to leave 1.1 g of an off white solid (5.6 mmol, yield 99%) that was used without further purification.

Description 11: 3-Methoxy4-[2-[(4,5-dichloro-2-nitro)phenyl]-1-oxo-ethyl]-benzonitrile

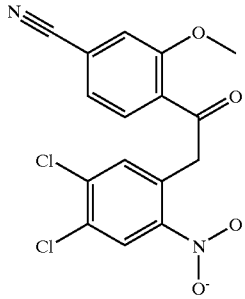

2-Methoxy-4-cyanobenzoyl chloride (1.1 g, 5.6 mmol) was added portionwise to a stirred solution of trans-4,5-dichloro-2-nitro-β-dimethylaminostyrene (1.47 g, 5.6 mmol) and triethylamine (1.5 ml, 10 mmol) in cyclohexane (20 ml). The solution was then refluxed for 16 h. The reaction was cooled and all the volatile products removed using a rotary evaporator. A dark residue was obtained which was then dissolved in is CH₂Cl₂ (40 ml) and washed once with 10% Na₂CO₃ solution (20 ml). The organic layer was then dried with anhydrous Na₂SO₄, filtered and the solvent removed using a rotary evaporator. Dark brown to black powder (2.42 g) was obtained that was dissolved in as little ethyl acetate as possible and hexane was added to this solution to precipitate light brown powder (1.72 g, mp=167–170° C.) that was used without further purification in the next step.

This crude intermediate (1.2 g) was dissolved in 1,4-dioxane (20 ml) and water (10 ml) was added. The solution was refluxed for 48 h, filtered while still hot and then chilled in an ice water bath. Yellow to brown crystals were collected on a buchner funnel obtaining 0.60 g (1.6 mmol, yield 30%) of the title compound. mp=171–174° C.

¹H NMR(CDCl₃) δ=8.27 (s, 1H); 7.81 (d, 1H); 7.49 (s, 1H); 7.35 (dd, 1H); 7.28 (d, 1H); 4.61 (s, 2H); 4.00 (s, 3H).

Description 12: 3-Methoxy-4-(5,6-dichloro-1H-indol-2-yl)-benzonitrile

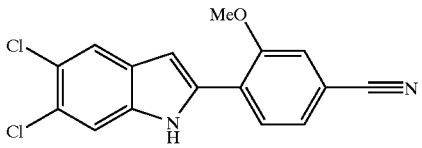

3-Methoxy-4-[2-(4,5-dichloro-2-nitro)phenyl-1-oxo-ethyl]-benzonitrile (0.4 g, 1.0 mmol) was dissolved in EtOH (10 ml) and AcOH (10 ml). The solution was brought to gently reflux and iron powder (0.5 g, 9 mmol) was added in small portions over the period of an hour. The solution was refluxed for 12 h after which the solvents were removed using a rotary evaporator. The residue was extracted several times with THF. After removal of the solvent, crude 3-methoxy-4-(5,6-dichloro-1H-indol-2-yl)-benzonitrile (0.35 g, 1.0 mmol, yield 100%) was obtained that was used in the next step without further purification mp=241–244° C.

$^1$H NMR(DMSO-$d_6$) δ=11.60 (s br, 1H); 7.98 (d, 1H); 7.85 (s, 1H); 7.67 (s, 1H); 7.65 (d, 1H); 7.55 (dd, 1H); 7.14 (s, 1H); 4.00 (s, 3H).

Description 13: 3-Methoxy-4-(5,6-dichloro-1H-indol-2-yl)-benzoic acid

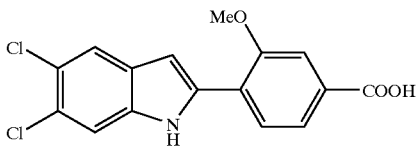

3-Methoxy-4-(5,6-dichloro-1H-indol-2-yl)-benzonitrile (0.35 g, 1.0 mmol) was suspended in 30% NaOH (20 ml) and 95% EtOH (20 ml). The mixture was refluxed for 12 h and then allowed to cool to room temperature. The suspension was concentrated to about half volume using a rotary evaporator and then filtered on a buchner funnel obtaining a tan to yellow coloured powder. This was stirred for 2 hour in 10% HCl. The solution was then filter to yield 0.256 g (0.76 mmol. yield 69%) of the crude title compound that was purified by chromatography to yield 150 mg of pure title compound, mp>270° C.

$^1$H NMR(DMSO-$d_6$) δ=11.60 (broad s, 1H); 7.92 (d, 1H); 7.83 (s, 1H); 7.66 (m, 3H); 7.10 (s, 1H); 4.02 (s, 3H).

Description 14: 2-(5,6-Dichloro-1H-indol-2-yl)benzoic acid

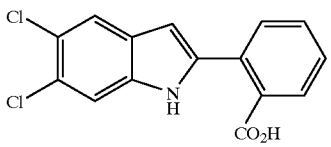

Starting from trans-4,5-dichloro-2-nitro-β-dimethylaminostyrene and 2-(methoxycarbonyl)benzoyl chloride and following successively the procedures of Descriptions 2, 3 and 4 afforded the title compound as a light brown solid which was used without further purification in the next step.

$^1$H-NMR(DMSO-$d_6$) δ=11.71 (s, 1H); 7.82 (s, 1H); 7.76 (d, 1H); 7.65–7.52 (m, 4H); 6.54 (s, 1H) ppm.

Description 15: 3-(5,6-Dichloro-1H-indol-2-yl)benzoic acid

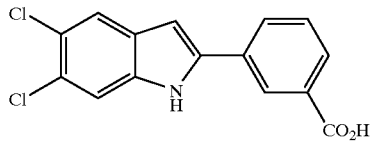

Starting from trans-4,5-dichloro-2-nitro-β-dimethylaminostyrene and 3-(methoxycarbonyl)benzoyl chloride and following successively the procedures of Descriptions 2, 3 and 4 afforded the title compound as a beige solid which was used without further purification in the next step.

$^1$H-NMR(DMSO-$d_6$) δ=12.06 (s, 1H); 8.43 (s, 1H); 8.12 (d, 1H), 7.93 (d, 1H); 7.82 (s, 1H); 7.66–7.58 (m, 2H); 7.02 (s, 1H) ppm.

Example 1

4-(5,6-Dichloro-1H-indol-2-yl)-N-(1,2,2,6,6-pentamethypiperidin-4-yl)benzamide

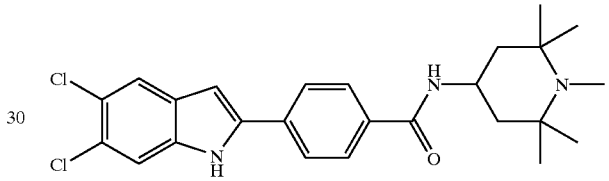

A mixture of) of 4-(5,6-dichloro-1H-indol-2-yl) benzoic acid (0.25 g, 0.82 mmol), WSC (0.156 g, 0.82 mmol), HOAT (0.11 g, 0.82 mmol), 4-amino-1,2,2,6,6-pentamethylpiperidine (0.209 g, 1.2 mmol), DIEA (0.212 g, 1.2 mmol) in DMF (3 ml) was stirred at room temperature for 16 h. The mixture was then poured on water, made basic by NaOH N and extracted with ethyl acetate. The organic solution was washed with water, dried over $MgSO_4$, concentrated in vacuo, and the residue was purified by column chromatography ($SiO_2$, $CH_2Cl_2/CH_3OH/NH_4OH$; 9/1/0.1), affording 0.35 g (0.76 mmol, yield 93%) of the title compound as white crystals, mp=325° C.

$^1$H-NMR(DMSO-$d_6$) δ=11.98 (s, 1H); 8.26 (d, 1H); 7.95 (m,4H); 7.82 (s, 1H); 7.6 (s, 1H); 7.05 (s, 1H); 4.19 (m, 1H); 2.19 (s, 3H); 1.71 (m, 2H); 1.48 (m, 2H); 1.10 (s, 6H); 1.05 (s, 6H).

Example 2

4-(5,6-Dichloro-1H-indol-2-yl)-3-methoxy-N-(1,2,2,6,6-pentamethylpiperidin-4yl)-benzamide

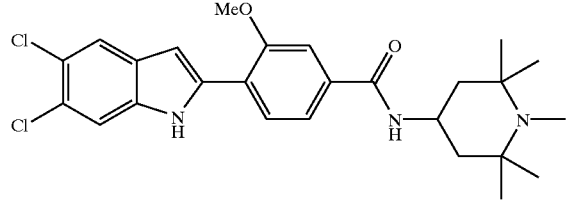

A mixture of 3-methoxy-4-(5,6-dichloro-1H-indol-2-yl)-benzoic acid (0.15 g, 0.45 mmol), WSC (0.094 g, 0.5 mmol), HOAT (0.067 g, 0.5 mmol), 4-amino-1,2,2,6,6-pentamethylpiperidine (0.15 g, 0.9 mmol) in DMF (2 ml) was stirred at 50° C. for 18 h. The mixture was then poured in a large volume of water and extracted with AcOEt. The organic phase was washed with water, dried over $MgSO_4$ and concentrated in vacuo. The residue was purified by flash chromatography ($SiO_2$; $CH_2Cl_2$—MeOH—$NH_4OH$: 91.5-7.5-1) then crystallised in di-isopropyl ether to afford 0.13 g (0.26 mmol. yield 59%) of the title compound, mp=260° C.

$^1H$ NMR(DMSO-$d_6$) δ=11.58 (s, 1H); 8.26 (d, 1H); 7.88 (d, 1H); 7.82 (s, 1H); 7.67 (s, 1H); 7.57 (m, 2H); 7.07 (s, 1H); 4.22 (m, 1H); 4.02 (s, 3H); 2.20 (s, 3H); 1.73 (m, 2H); 1.46 (m, 2H); 1.11 (s, 6H); 1.06 (s, 6H).

Example 3

4-(5,6-Dichloro-1H-indol-2-yl)-2-methoxy-N-(1,2,2,6,6-pentamethylpiperidin-4-yl)-benzamide

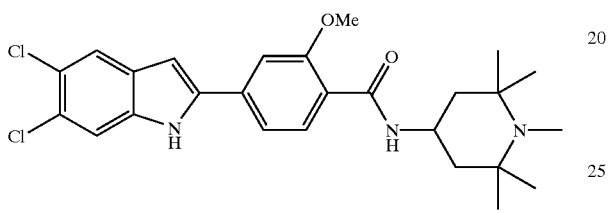

This compound was obtained by the same procedure starting from the corresponding 2-methoxy-4-(5,6-dichloro-1H-indol-2-yl)-benzoic acid.

$^1H$ NMR(DMSO-$d_6$) δ=11.98 (s, 1H); 7.91 (d, 1H); 7.82 (s, 1H); 7.77 (d, 1H); 7.56 (m, 3H); 7.08 (s, 1H); 4.19 (m, 1H); 4.00 (s, 3H); 2.19 (s, 3H); 1.75 (m, 2H); 1.38 (m, 2H); 1.10 (s, 6H); 1.05 (s, 6H).

Example 4

2-(5,6-Dichloro-1H-indol-2-yl)-N-(3-dimethylaminopropyl)benzamide

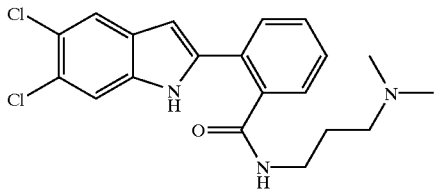

A mixture of crude 2-(5,6-dichloro-1H-indol-2-yl) benzoic acid (0.19 g, 0.62 mmol), WSC (0.13 g, 0.68 mmol), HOAT (0.093 g, 0.68 mmol), dimethylamino propylamine (0.13 g, 1.3 mmol) in DMF (2 ml) was heated at 50° C. for 16 h. The mixture was then poured on water and extracted with ethyl acetate. The organic phase was washed twice with water, dried over $MgSO_4$, concentrated in vacuo and the residue was purified by column chromatography ($SiO_2$, $CH_2Cl_2/CH_3OH/NH_4OH$; 9/1/0.1) to afford the title compound as an oil, which crystallised by trituration in diisopropyl ether obtaining, after filtration, 0.072 g (0.18 mmol yield 30%) of the title compound as white crystals, mp=169° C.

$^1$H-NMR (DMSO-$d_6$) δ=11.63 (s, 1H); 8.32 (t, 1H); 7.79 (s, 1H); 7.69 (d, 1H); 7.61 (s, 1H); 7.59–7.35 (m, 3H); 6.62 (s, 1H); 3.18 (m, 2H); 2.08 (t, 2H); 2.00 (s, 6H); 1.49 (m, 2H).

Example 5

3-(5,6-Dichloro-1H-indol-2-yl)-N-(3-dimethylaminopropyl)benzamide

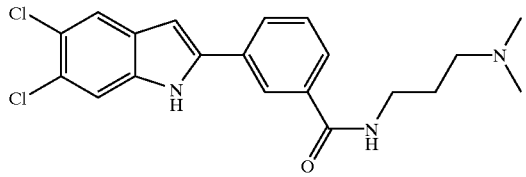

The title compound was obtained as a white solid (mp=204° C.) starting from 3-(5,6-dichloro-1H-indol-2-yl) benzoic acid and following the procedure described above.

$^1$H-NMR (DMSO-$d_6$) δ=12.00 (s, 1H); 8.63 (t, 1H); 8.31 (s, 1H); 7.99 (d, 1H); 7.83 (s, 1H); 7.78 (d, 1H); 7.60 (s, 1H); 7.57 (t, 1H); 7.00 (s,1H); 3.28 (t, 2H); 2.27 (t, 2H); 2.14 (s, 6H); 1.68 (m, 2H).

The following compounds were prepared according to the procedure of Example 1

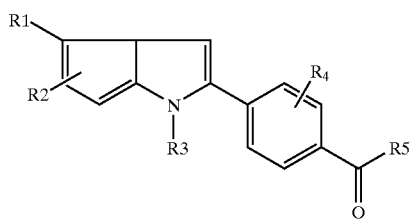

| Ex. No | Name | R1 | R2 | R3 | R4 | R5 |
|--------|------|----|----|----|----|----|

-continued

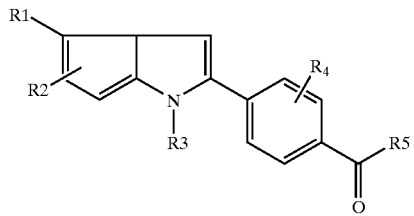

| | | R1 | R2 | R3 | R4 | R5 |
|---|---|---|---|---|---|---|
| 6 | 4-(5,6-Dichloro-1H-indol-2-yl)-3-methoxy-N-(3-diethylaminopropyl)-benzamide. | —Cl | —Cl | —H | 2-OMe | 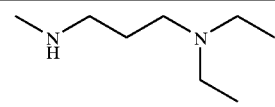 |
| 7 | 4-(5,6-Dichloro-1H-indol-2-yl)-3-methoxy-N-[3-[4-(3-chlorophenyl)piperazinyl]propyl]-benzamide. | —Cl | —Cl | —H | 2-OMe | 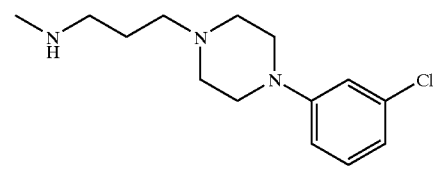 |
| 8 | 4-(5,6-Dichloro-1H-indol-2-yl)-3-methoxy-N-[3-[4-(3-hydroxyphenyl)piperazinyl]propyl]-benzamide. | —Cl | —Cl | —H | 2-OMe | 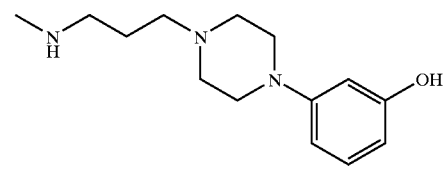 |
| 9 | 4-(5,6-Dichloro-1-methyl-1H-indol-2-yl)-3-methoxy-N-(1,2,2,6,6-pentamethylpiperidin-4-yl)-benzamide | —Cl | —Cl | —Me | 2-OMe | 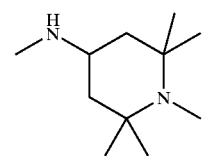 |
| 10 | 4-(5,6-Dichloro-1-methyl-1H-indol-2-yl)-3-methoxy-N(1,2,2,6,6-pentamethylpiperidin-4-yl)-N-methylbenzamide | —Cl | —Cl | —Me | 2-OMe | 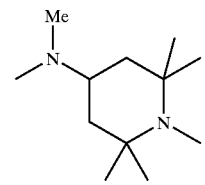 |
| 11 | 4-(5,6-Dichloro-1H-indol-2-yl)-3-methoxy-N-(2,2,6,6-tetramethylpiperidin-4-yl)-N-methylbenzamide | —Cl | —Cl | —H | 2-OMe | 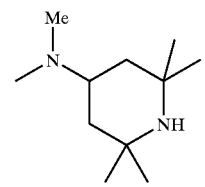 |

| Ex. No | MP ° C. | N.M.R. |
|---|---|---|
| 6 | 128–135 | $^1$H—NMR(DMSO-d$_6$) δ = 11.30(s br, 1H); 8.30(t br, 1H); 7.84(d, 1H); 7.77(s, 1H); 7.67(s, 1H); 7.58(d, 1H); 7.53(dd, 1H); 7.02(s, 1H); 4.02(s, 3H); 3.35(dt, 1H); 2.52(q, 4H); 2.51(t, 2H); 1.72(dt, 2H), 0.99(t, 6H). |
| 7 | 146–148 | $^1$H—NMR(DMSO-d$_6$) δ = 11.43(s br, 1H); 8.57(t br, 1H); 7.88(d, 1H); 7.81(s, 1H); 7.66(s, 1H); 7.61(s, 1H); 7.56(d, 1H); 7.20(t, 1H); 7.06(s, 1H); 6.94(s, 1H); 6.90(d, 1H); 6.78(d, 1H); 4.02(s, 3H); 3.42–3.15(m, 6H); 2.60-240(m, 6H); 1.77(m, 2H). |
| 8 | 180–182 | $^1$H—NMR(DMSO-d$_6$) δ = 11.50(s, 1H); 9.02(s, 1H); 8.55(t br, 1H); 7.88(d, 1H); 7.80(s, 1H); 7.65(s, 1H); 7.60(s, 1H); 7.58(d, 1H); 7.05(s, 1H); 6.96(dd, 1H); 6.37(d, 1H); 6.30(s, 1H); 6.70(d, 1H); 4.00(s, 3H); 3.39–3.31(m, 2H); 3.10(m, 4H); 2.50(m, 4H); 2.40(t, 2H); 1.75(m, 2H). |
| 9 | 136–141 | $^1$H—NMR(DMSO-d$_6$ at 353K) δ = 7.92(d br, 1H); 7.79(s, 1H); 7.74(s, 1H); 7.60(d, 1H); 7.58(dd, 1H); 7.40(d, 1H); 6.49(s, 1H); |

-continued

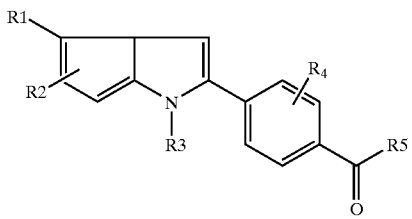

| | | |
|---|---|---|
| | | 4.30–4.22(m, 1H); 3.89(s, 3H); 3.54(s, 3H); 2.25(s, 3H); 1.80(dd, 2H); 1.50(dd, 2H); 1.13(s, 6H); 1.10(s, 6H). |
| 10 | 195–200 | $^1$H—NMR(DMSO-$d_6$) δ = 7.78(s, 1H); 7.72(d, 1H); 7.40(d, 1H); 7.14(d, 1H) 7.03(dd, 1H); 6.48(s, 1H); 4.25–4.10(m, 1H); 3.81(s, 3H); 3.55(s, 3H); 2.90(s, 3H); 2.19(s, 3H); 1.70(dd, 2H); 1.59(dd, 2H); 1.10(s, 6H); 0.88(s br, 6H). |
| 11 | 223–226 | $^1$H—NMR(DMSO-$d_6$ at 333K) δ = 11.35(s br, 1H); 7.85(d, 1H); 7.76(s, 1H); 7.65(s, 1H); 7.13(d, 1H); 7.03(dd, 1H); 6.98(s, 1H); 3.98(s, 3H); 2.84(s, 3H); 1.54(dd, 2H); 1.41(dd, 2H); 1.06(s br, 13H). |

Biological Assays

Background. It is known that, upon attachment to bone, an electrogenic H$^+$—adenosine triphosphatase (ATPase) is polarised to the osteoclast-bone interface. The pump transports massive quantities of protons into the resorption microenvironment to effect mobilisation of the bone mineral and to create the acidic pH required by collagenases to degrade the bone matrix.

The vacuolar nature of the osteoclast proton pump was originally recognised by Blair [H. C. Blair at al., *Science*, 245, 855 (1989)] and than confirmed by Bekker [P. J. Bekker et al., *J Bone Min. Res.*, 5, 569 (1990)] and Väänänen [H. K. Väänänen et al., *J Cell. Biol*, 111, 1305 (1990)]. Evidence was based upon preparations of ruffled membrane fragments from avian osteoclasts (obtained from the medullar bone of calcium-starved egg-laying hens). The resulting membrane vesicles acidify in response to ATP, which is easily assessed by measuring the fluorescence quench of acridine orange, a weak base which accumulates into acidic compartments.

The biochemical pattern indicated that the osteoclast proton pump belonged to the vacuolar-like ATPases since proton transport was inhibited by N-ethylmaleimide (NEM), a sulphydryl reagent, and by bafilomycin $A_1$, a selective inhibitor of vacuolar H$^+$-ATPases [J. E. Bowman et al., *Proc. Natl. Acad Sci. USA*, 85, 7972 (1988)], whilst it was not inhibited by ouabain, an inhibitor of Na$^+$/K$^+$-ATPases; sodium orthovanadate, an inhibitor of P-ATPases, or by omeprazole or SCH 28080, both of which are inhibitors of gastric H$^+$/K$^+$-ATPase [J. P. Mattsson et al., *Acta Physiol. Scand.*, 146, 253 (1992)].

It is known that specific inhibitors of vacuolar ATPases, such as bafilomycin $A_1$, are able to inhibit bone resorption in osteoclast cultures [K. Sundquist et al., *Biochem. Biophys. Res. Commun.* 168, 309–313 (1990)]

Inhibition of Proton Transport and v-ATPase Activity in Membrane Vesicles

Preparation of Crude Bone Microsomes from Calcium-starved Egg-laying Hens

Vesicles were prepared from medullar bone obtained from tibiae and femurs or egg-laying hens which were calcium-starved for at least 15 days. Briefly, bone fragments were scraped with a 24 scalpel blade, suspended in 40 ml of isolation medium (0.2 M sucrose, 50 mM KCl, 10 mM Hepes, 1 mM EGTA, 2 mM dithiotheitrol, pH 7.4) and filtered through a 100 μm pore size nylon mesh. The whole procedure was performed at 4° C. After homogenisation in a potter (20 strokes) in 40 ml of isolation medium an initial centrifugation (6,500×$g_{max}$×20 min) was performed to remove mitochondria and lysosomes. The supernatant was centrifuged at 100,000×$g_{max}$ for 1 hr and the pellet was collected in 1 ml of isolation medium, divided into 200 μl aliquots, immediately frozen in liquid nitrogen and stored at −80° C. The protein content was determined using a Biorad colourimetric kit according to Bradford [M. Bradford, *Anal. Biochem.*, 72, 248 (1976)]. For the proton transport assay, 5–10 μl of membranes were used.

Purification of osteoclast membranes. 1 ml of crude microsomal vesicles prepared above were applied (about 0.2 ml per tube ) on the top of a sucrose step-gradient consisting of 3.5 ml of 15%, 30% and 45% (w/w) sucrose in isolation medium and centrifuged at 280,000 $g_{max}$ for 2 h (SW 41 Ti rotor). After centrifugation the 30–45% sucrose interfaces were collected, diluted approx. 20-fold in isolation medium and pelletted at 100,000 $g_{max}$ for 1 hour (SW 28 rotor). The pellet was then resuspended in 1 ml of isolation medium, aliquoted and frozen in liquid $N_2$ and stored at −80° C. until used.

Human kidney membranes were obtained from the cortex of a human kidney, frozen immediately after surgery, according to the method reported in the literature for bovine kidney (S. Gluck, *J Biol. Chem.*, 265, 21957 (1990)).

Preparation of human osteoclast microsomal vesicles. Osteoclast-like giant cells isolated from osteoclastoma tumor were homogenized with a glass-teflon homogenizer (1000 rpm×20 strokes), and the material was centrifuged at 6000×$g_{max}$ for 20 minutes. The resulting pellet was then spun at 100000×$g_{max}$ for 60 minutes to pellet the microsomal fraction. Resuspended in 1 ml of isolation medium pH 7.4. frozen by liquid nitrogen immersion and stored at −80° C. until used.

Proton transport in membrane vesicles was assessed. semi-quantitatively, by measuring the initial slope of fluorescence quench of acridine orange (excitation 490 nm; emission 530 nm) after addition of 5–20 μl of membrane vesicles in 1 ml of buffer containing 0.2 M sucrose, 50 mM KCl, 10 mM Hepes pH 7.4. 1 mM ATP.Na2, 1 mM CDTA, 5 μM valinomycin and 4 μM acridine orange. The reaction was started by addition of 5 mM MgSO4. Results were expressed as the percent of the mean of two controls.

Inhibition of bafilomycin-sensitive ATPase activity was assessed in purified membrane vesicles by measuring the release of inorganic phosphate (Pi) during 30 min of incubation at 37° C. in a 96-well plate either in the presence or in the absence of bafilomycin A1. The reaction medium contained 1 mM ATP, 10 mM HEPES-Tris pH 8, 50 mM KCl, 5 uM valinomycin, 5 uM nigericin, 1 mM CDTA-Tris, 100 uM ammonium molybdate, 0.2 M sucrose and membranes (20 ug protein/ml). The reaction was initiated by $MgSO_4$ (8-arm pipette) and stopped, after 30 min, by addition of 4 volumes of the malachite green reagent (96-arm pipette) prepared according to Chan [*Anal. Biochem.* 157, 375 (1986)]. Absorbance at 650 nm was measured after 2 min using a microplate reader. Results are expressed as nmol (Pi)×mg protein$^{-1}$×min$^{-1}$ and, for each experiment, represent the mean±sem of triplicates.

Pharmacological Data

Compounds described in the present invention are able to inhibit bafilomycin-sensitive ATPase of chicken osteoclast in a range from 50 nM to 2 $\mu$M and of human osteoclast in a range from 30 nM to 5 $\mu$M. An example of these results is shown below:

| Ex. No | IC$_{50}$ ($\mu$M) ATPase assay |
|---|---|
| 1 | 0.35 |
| 2 | 0.096 |
| 3 | 1.3 |

Inhibition of Bafilomycin-sensitive ATPase in Human Osteoclast and Human Kidney Membranes

| Ex No | IC$_{50}$ h osteoclast | IC$_{50}$ h kidney |
|---|---|---|
| 1 | 0.25 | 1.25 |
| 2 | 0.126 | 0.2 |

What is claimed is:

1. A compound of formula (I):

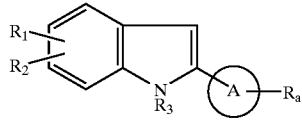

(I)

or a salt thereof, or a solvate thereof, wherein:

A is an unsubstituted or substituted aryl group;

$R_a$ represents —CO—$NR_sR_t$ wherein $R_s$ and $R_t$ each independently represent hydrogen; alkyl, substituted alkyl, unsubstituted or substituted alkenyl, unsubstituted or substituted aryl, unsubstituted or substituted arylalkyl, unsubstituted or substituted heterocyclyl or an unsubstituted or substituted heterocyclylalkyl group, or $R_s$ and $R_t$ together with the nitrogen to which they are attached form a heterocyclyl group;

$R_1$ and $R_2$ each independently represents a halogen;

$R_3$ represents hydrogen, alkanoyl, alkyl, aminoalkyl, hydroxyalkyl, carboxyalkyl, carbalkoxyalkyl, carbamoyl, alkylsulphonyl, or arylsulphonyl;

in which each heterocyclyl group independently is a saturated or unsaturated single or fused ring heterocyclic group, each ring having 5 to 8 ring atoms which ring atoms include 1, 2 or 3 heteroatoms selected from O, S, or N; and in which each substituted group independently contains up to 3 substitutents selected from alkyl, alkoxy, thioalkyl, hydroxy, halogen, trifluoromethyl, alkylcarbonyl, cyano, nitro and $NR_uR_v$, wherein $R_u$ and $R_v$ each independently represent hydrogen, alkyl and alkylcarbonyl.

2. A compound according to claim 1, wherein $R_1$ is 5-chloro, and $R_2$ is 6-chloro.

3. A compound according to claim 1, wherein $R_3$ represents hydrogen.

4. A compound according to claim 1, wherein $R_s$ and $R_t$ each independently represent $C_{1-6}$ alkyl groups.

5. A compound according to claim 1, wherein $R_s$ represents an unsubstituted or substituted heterocyclyl or aryl.

6. A compound according to claim 1, wherein $R_s$ represents an unsubstituted or substituted piperidinyl group.

7. A compound according to claim 1, wherein $R_s$ represents 1,2,2,6,6-pentamethylpiperidin-4-yl group or 2,2,6,6-tetramethylpiperidin-4-yl.

8. A compound according to claim 1, wherein $R_s$ represents an unsubstituted or substituted heterocyclylalkyl group.

9. A compound according to claim 8, wherein $R_s$ represents an unsubstituted or substituted piperazinyl-$C_{1-6}$alkyl group.

10. A compound according to claim 8, wherein the substituents for the heterocyclyl group are selected from: hydroxyphenyl or chlorophenyl groups.

11. A compound according to claim 1, wherein $R_t$ represents hydrogen.

12. A compound selected from:

4-(5,6-dichloro-1H-indol-2-yl)-N-(1,2,2,6,6-pentamethypiperidin-4-yl)benzamide;

4-(5,6-dichloro-1H-indol-2-yl)-3-methoxy-N-(1,2,2,6,6-pentamethylpiperidin-4-yl)-benzamide;

4-(5,6-dichloro-1H-indol-2-yl)-2-methoxy-N-(1,2,2,6,6-pentamethylpiperidin-4-yl)-benzamide;

2-(5,6-dichloro-1H-indol-2-yl)-N-(3-dimethylaminopropyl) benzamide;

3-(5,6-dichloro-1H-indol-2-yl)-N-(3-dimethylaminopropyl) benzamide;

4-(5,6-dichloro-1H-indol-2-yl)-3-methoxy-N-(3-diethylaminopropyl)-benzamide;

4-(5,6-dichloro-1H-indol-2-yl)-3-methoxy-N-[3-[4-(3-chlorophenyl)piperazinyl]propyl]-benzamide;

4-(5,6-dichloro-1H-indol-2-yl)-3-methoxy-N-[3-[4-(3-hydroxyphenyl)piperazinyl]propyl]-benzamide;

4-(5,6-dichloro-1-methyl-1H-indol-2-yl)-3-methoxy-N-(1,2,2,6,6-pentamethylpiperidin-4-yl)-benzamide;

4-(5,6-dichloro-1-methyl-1H-indol-2-yl)-3-methoxy-N-(1,2,2,6,6-pentamethylpiperidin-4-yl)-N-methylbenzamide; and 4-(5,6-dichloro-1H-indol-2-yl)-3-methoxy-N-(2,2,6,6-tetramethylpiperidin-4-yl)-N-methylbenzamide; or a salt thereof, or a solvate thereof.

13. A process for preparing a compound of formula (I) or a salt thereof or a solvate thereof according to claim 1, which process comprises amidating a compound of formula (II):

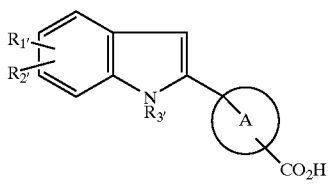

(II)

wherein A is as defined in relation to formula (I), $R_{1'}$, $R_{2'}$ and $R_{3'}$ each respectively represent $R_1$, $R_2$ and $R_3$ as defined in relation to formula (c) or a protected form thereof; and thereafter, as necessary, carrying out one or more of the following reactions:

(i) removing any protecting group;

(ii) preparing a salt or a solvate of the compound so formed.

14. A pharmaceutical composition comprising a compound of formula (I) according to claim 1, or a pharmaceutically acceptable salt thereof, or a pharmaceutically acceptable solvate thereof, and a pharmaceutically acceptable carrier therefor.

15. A method for the treatment of osteoporosis and related osteopenic diseases in a human or non-human mammal, which comprises administering an effective, non-toxic, amount of a compound of formula (I) according to claim 1 or a pharmaceutically acceptable solvate thereof, to a human or non-human mammal in need thereof.

* * * * *